US00PP28779P2

(12) United States Plant Patent
Van Swieten

(10) Patent No.: US PP28,779 P2
(45) Date of Patent: Dec. 19, 2017

(54) ***PHALAENOPSIS* ORCHID PLANT NAMED 'PHALCISYP'**

(50) Latin Name: ***Phalaenopsis* hybrid**
Varietal Denomination: PHALCISYP

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/330,574

(22) Filed: Oct. 13, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALCISYP', particularly characterized by having light yellow-green flowers with red-purple lips, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALCISYP'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALCISYP'.

The new *Phalaenopsis* plant is a product of a planned breeding program conducted by the inventor in Bleiswijk, The Netherlands. The objective of this breeding program was to create a new *Phalaenopsis* plant with light yellow-green flowers and red-purple lips, suitable for potted plant production.

The new *Phalaenopsis* plant 'PHALCISYP' is a result of cross-pollination made by the inventor in February 2002 in Bleiswijk, The Netherlands of the proprietary female, or seed parent, *Phalaenopsis* hybrid '06733-0001' (unpatented) with the proprietary male, or pollen parent, *Phalaenopsis* hybrid '20064-0001' (unpatented).

The new *Phalaenopsis* was selected by the inventor as a single plant within the progeny of the stated cross-pollination in a controlled greenhouse in Bleiswijk, The Netherlands in December 2005. Asexual reproduction of the new *Phalaenopsis* plant by meristem tissue culture since 2010 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALCISYP' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALCISYP' as a new and distinct variety of *Phalaenopsis* plant.

1) Light yellow-green flowers with red-purple lips;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in August 2016. Colors in the photographs may differ from the color values cited in the detailed botanical description, which accurately describe the actual colors of the new variety.

DESCRIPTION OF THE NEW VARIETY

Figure 1:
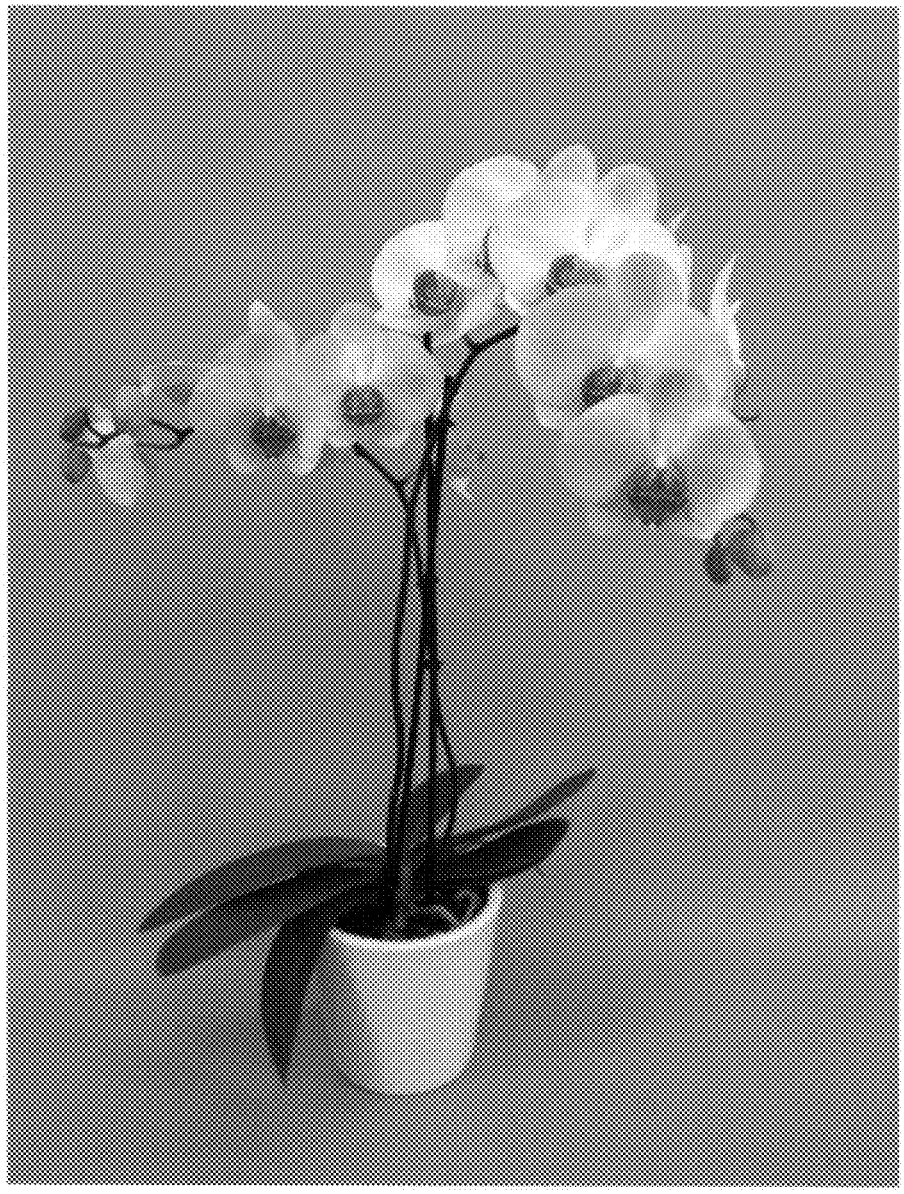
FIG. 1 shows the overall plant habit, including blooms, buds and foliage of 'PHALCISYP'.
Figure 2:
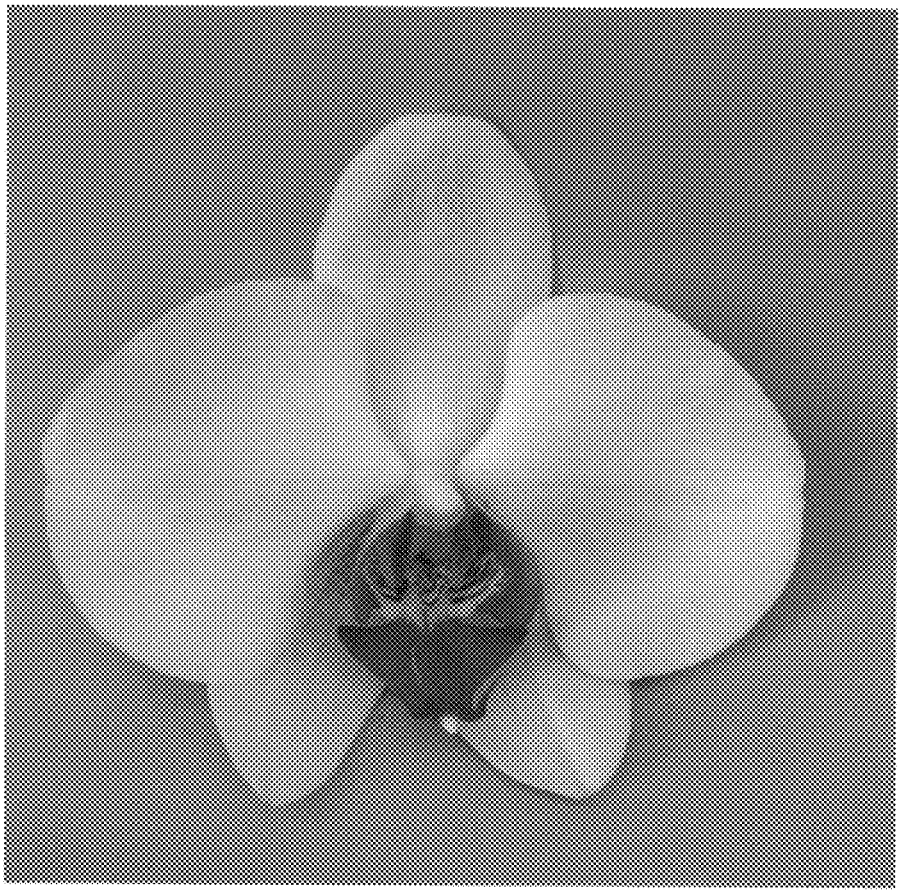
FIG. 2 shows a close-up of a flower of 'PHALCISYP'.
Figure 3:
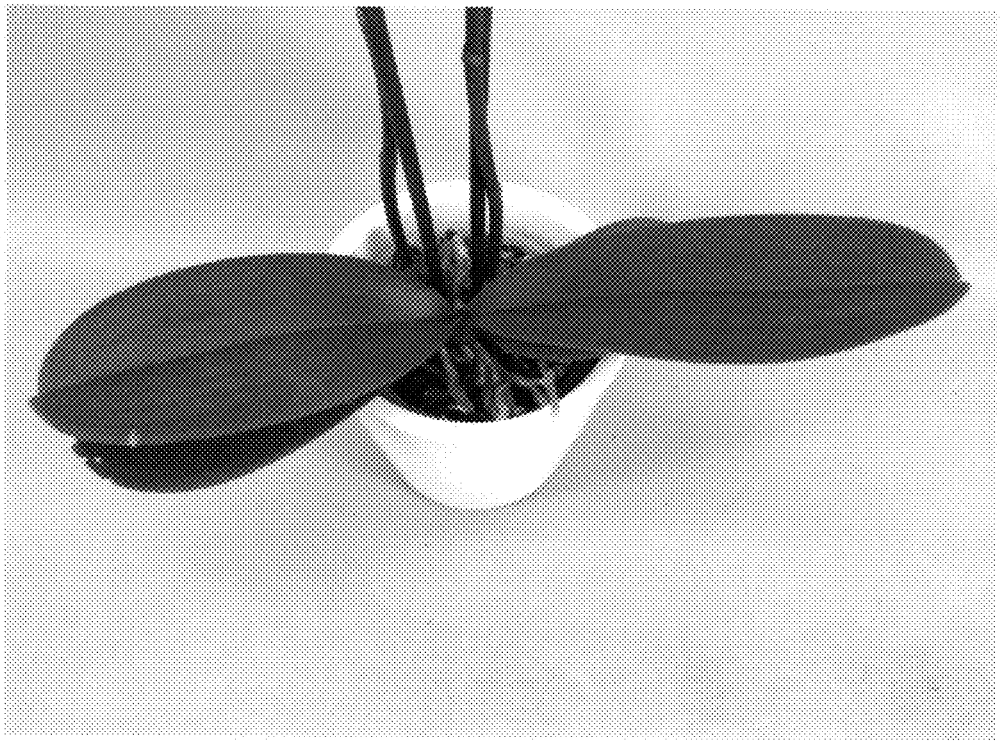
FIG. 3 shows a close-up of the leaves of 'PHALCISYP'.

The following detailed description sets forth the distinctive characteristics of 'PHALCISYP'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in August 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALCISYP'.

Parentage:

*Female parent*.—*Phalaenopsis* cultivar '06733-0001' (unpatented).

*Male parent*.—*Phalaenopsis* cultivar '20064-0001' (unpatented).

Propagation:

*Type*.—Meristem tissue culture.

Roots:

*Root description*.—Greyed-green colored roots with branching lateral roots having light purple colored root tips.

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 50.0 cm to 55.0 cm.

*Width* (*measured from leaf tips*).—About 37.0 cm to 42.0 cm.

*Vigor*.—Strong.

Leaves:

*Mature leaves*.—Quantity per plant: 7 to 9 leaves are produced before flowering. Length (fully expanded): 18.0 cm to 20.0 cm. Width: 7.0 cm to 8.0 cm. Shape: Oblong. Base shape: Moderately elongated. Apex: Unequal obtuse. Leaf blade angle with the petiole (measured from the horizontal position): Between 10 degrees and 20 degrees. Leaf margin: Entire. Color: Upper surface: RHS 146B. Lower surface: RHS 144A. Texture: Rough. Thickness: 2.2 mm to 2.4 mm. Venation: Pattern: Parallel. Color of the mid-vein: Upper surface: RHS 146C. Lower surface: RHS 146B.

Peduncle:

*Quantity per plant*.—1 to 3.

*Number of flowers per peduncle*.—11 to 14.

*Length*.—55.0 cm to 65.0 cm.

*Diameter*.—5.2 mm to 5.6 mm.

*Strength*.—Strong.

*Aspect*.—Upright to slightly pendant.

*Texture*.—Smooth.

*Color*.—Brown (RHS 200B) with a touch of green (RHS 146B).

*Internode length*.—25.0 mm to 35.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 230.0 mm to 260.0 mm.

*Flowering time*.—First flowers can be expected 10 to 11 months after planting in a 12 cm (diameter) pot.

*Flower*.—Height: 82.0 mm to 87.0 mm. Diameter: 88.0 mm to 93.0 mm. Depth of lip: 23.0 mm to 25.0 mm.

*Flower longevity*.—On the plant: 9 to 13 weeks.

*Fragrance*.—Absent.

*Flower bud*.—Average size: Large. Length: 27.0 mm to 29.0 mm. Width: 22.0 mm to 24.0 mm. Shape: Egg shaped. Color: Light green (RHS 150C) with a touch of light purple (RHS N78D).

*Petals*.—Arrangement: Open/free. Shape: Semi-circular. Apex: Rounded asymmetric. Margin: Entire. Length (from base to tip): 44.0 mm to 46.0 mm. Width: 54.0 mm to 56.0 mm. Color (when fully opened): Upper surface: Basic color: Light yellow-green (RHS 150D). Over color: Diluted light purple (RHS 61A) at the base and white (RHS NN155C) at the center. Lower surface: Basic color: Light yellow-green (RHS 150D). Over color: White at the base (RHS NN155C).

*Dorsal sepal*.—Shape: Elliptic. Apex: Emarginated and symmetric. Margin: Entire. Length (from base to tip): 45.0 mm to 47.0 mm. Width: 31.0 mm to 33.0 mm. Color (when fully opened): Upper surface: Basic color: Light yellow-green (RHS 150D). Over color: White (RHS 154C) at the base. Lower surface: Basic color: Light yellow-green (RHS 150D). Over color: Light green (RHS 150D) and diluted light purple (RHS N78D).

*Lateral sepals*.—Shape: Ovate. Apex: Obtuse and asymmetric. Margin: Entire. Length (from base to tip): 47.0 mm to 49.0 mm. Width: 27.0 mm to 29.0 mm. Color (when fully opened): Upper surface: Basic color: Light yellow-green (RHS 150D). Over color: Light green (RHS 150C) and dotted at the base (RHS 183B). Lower surface: Basic color: Light yellow-green (RHS 150D). Over color: Light yellow-green (RHS 150C) and diluted light purple (RHS N78D).

*Labellum* (*lip*).—Whiskers: Present. Length of whiskers: 13.0 mm to 15.0 mm. Color of whiskers: Purple (RHS 71A) with yellow (RHS 5C) tips. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length (from base to tip): 20.0 mm to 22.0 mm. Width: 16.0 mm to 18.0 mm. Color: Purple (RHS N78C) and red-purple (RHS 60A) on the side; white (RHS NN155C) and striped (RHS 183B) at the base.

*Apical lobe*.—Shape: Triangular. Margin: Entire. Length: 26.0 mm to 28.0 mm. Width: 20.0 mm to 22.0 mm. Color: Purple (RHS N78A) towards the whiskers, red-purple (RHS 60A and 183C) and yellow (RHS 5C) towards the callus; white tip (RHS NN55C) between the whiskers.

*Callus*.—Average size: Medium to large. Height: 0.4 cm to 0.6 cm. Length: 0.6 cm to 0.8 cm. Width: 0.4 cm to 0.6 cm. Color: Yellow (RHS 2A and 2D) and dotted (RHS 183B).

*Reproductive organs*.—Column: Length: 8.0 mm to 10.0 mm. Diameter: 5.5 mm to 5.7 mm. Color: White (RHS NN155C). Pollinia: Quantity: 2. Diameter: 1.0 mm to 1.3 mm. Color: Orange (RHS 23A). Ovary: Length: 8.0 mm to 10.0 mm. Diameter: 2.3 mm to 2.5 mm. Pedicel: Length: 38.0 mm to 40.0 mm. Diameter: 2.8 mm to 3.0 mm. Color: Green (RHS 146C) at the base; light green (RHS 145C to 145D) to light purple (RHS N78D) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

The female parent of 'PHALCISYP', cultivar '06733-0001' (unpatented), is no longer in existence, so a meaningful comparison cannot be made.

The male parent of 'PHALCISYP', cultivar '20064-0001' (unpatented), is no longer in existence, so a meaningful comparison cannot be made.

'PHALCISYP' is most similar to the commercial *Phalaenopsis* plants named 'PHALFIMWAQ' (U.S. Plant Pat. No. 26,067) and '32892-03' (unpatented). 'PHALCISYP' differs from the commercial variety 'PHALFIMWAQ' in that 'PHALCISYP' has purple whiskers with yellow tips, a triangular apical lobe and a spatulate lateral lobe, whereas 'PHALFIMWAQ' has light yellow whiskers, a trullate apical lobe and a weakly spatulate lateral lobe. Additionally, 'PHALCISYP' has a wider apical lobe than 'PHALFIMWAQ'.

'PHALCISYP' differs from the commercial variety '32892-03' in that 'PHALCISYP' has light yellow-green flowers, purple whiskers with yellow tips, a triangular apical lobe, and a spatulate lateral lobe, whereas '32892-03' has yellow flowers, white whiskers, a rhombic apical lobe and an oblong to weakly spatulate lateral lobe. Additionally, 'PHALCISYP' has larger flowers and longer whiskers than '32892-03'.

I claim:

1. A new and distinct variety of *Phalaenopsis* plant named 'PHALCISYP', substantially as described and illustrated herein.

* * * * *